United States Patent
Wheeler et al.

(10) Patent No.: US 8,663,173 B2
(45) Date of Patent: Mar. 4, 2014

(54) DISPOSABLE SHIELD FOR A MEDICAL TOOL

(76) Inventors: Steve Wheeler, Victoria (CA); Al Wickheim, Sooke (CA)

( * ) Notice: Subject to any disclaimer, the term of this patent is extended or adjusted under 35 U.S.C. 154(b) by 162 days.

(21) Appl. No.: 13/320,006

(22) PCT Filed: Dec. 15, 2010

(86) PCT No.: PCT/IB2010/055825
§ 371 (c)(1),
(2), (4) Date: Nov. 10, 2011

(87) PCT Pub. No.: WO2011/073916
PCT Pub. Date: Jun. 23, 2011

(65) Prior Publication Data
US 2012/0157778 A1  Jun. 21, 2012

Related U.S. Application Data

(60) Provisional application No. 61/287,191, filed on Dec. 16, 2009.

(51) Int. Cl.
*A61M 5/32*  (2006.01)
(52) U.S. Cl.
USPC .......................................................... 604/192
(58) Field of Classification Search
USPC ................ 604/73, 268, 290, 294, 543, 192
See application file for complete search history.

(56) References Cited

U.S. PATENT DOCUMENTS

| | | | | |
|---|---|---|---|---|
| 1,934,046 A | * | 11/1933 | Demarchi | 604/115 |
| 5,947,894 A | * | 9/1999 | Chapman et al. | 600/119 |
| 6,071,640 A | | 6/2000 | Robertson, Jr. et al. | |
| 2002/0160728 A1 | | 10/2002 | Morita | |
| 2003/0091894 A1 | | 5/2003 | Hsueh | |
| 2010/0033125 A1 | | 2/2010 | Yamada | |
| 2011/0070473 A1 | | 3/2011 | Chen et al. | |

OTHER PUBLICATIONS

Combiguard II High Pressure Irrigation Splash Guard (ETHOX International) Feb. 1, 2008.*
Combiguard II High Pressure Irrigation Splash Guard (ETHOX International) Feb. 1, 2008 to Follow.

* cited by examiner

*Primary Examiner* — Theodore Stigell
(74) *Attorney, Agent, or Firm* — Davis & Bujold, PLLC; Michael J. Bujold

(57) ABSTRACT

A single use disposable shield and supportive stand for placement on a medical tool such as a suction catheter comprises a transparent body for protecting a responder from bodily fluids of a patient during suctioning of the oral or nasal cavities of a patient. As well the device acts as a supportive stand and securing agent for multiple medical devices and tools The body has an aperture for receiving a bushing. The bushing has an aperture for receiving the medical tool or device.

17 Claims, 6 Drawing Sheets

DISPOSABLE SHIELD FOR A MEDICAL TOOL

TECHNICAL FIELD

This invention pertains to surgical instruments and specifically to a disposable shield and stand for a medical tool or device.

BACKGROUND ART

Suction catheters are well known medical tools used as surgical instruments. One example is the 'Yankauer' suction catheter. This is a rigid hollow tube made of metal or disposable plastic with a curve at the distal end to facilitate the removal of thick pharyngeal secretions and other matter during oral pharyngeal suctioning and other medical procedures. Emergency room personnel and first responders and practitioners may be faced with having to clear the mouth or other natural or other cavities of blood, vomit, secretions and other bodily fluids. Therefore, there is a serious risk of infection to emergency room personnel and first responders from such diseases as HIV, H1N1 and Hepatitis B. Suctioning or irrigating of an oral or nasal cavity requires the responder to be in close contact with the patient and therefore there is at risk of being sprayed or splashed with contaminated fluids from an infected patient. Face shields and gloves provide limited protection to responders from such things as projectile vomiting. Therefore, there is an ongoing requirement to provide as much protection to the responder as possible when rendering assistance to patients with airway management needs and other procedures by shielding them from bodily fluids from being projected from oral and nasal cavities and other body systems during a suctioning procedure. To the best of our knowledge, prior art designs do not provide such shielding.

DISCLOSURE OF INVENTION

Technical Problem

Objects of the Invention

One object of the invention is to provide a shield for a medical tool.

Another objective of the invention is to provide support and securement for a medical tool or device.

Another object of the invention is to provide a shield for a suctioning instrument.

Another objective of the invention is to provide support and securement for a suctioning instrument.

Another object of the invention is to provide a shield for the Yankauer suctioning instrument.

Another objective of the invention is to provide support and securement for a Yankauer suctioning instrument.

Still another object of the invention is to provide a shield for a scalpel.

Another objective of the invention is to provide support and securement for a scalpel.

Another object of the invention is to provide a shield for a syringe.

Another objective of the invention is to provide support and securement for a syringe.

Yet another object of the invention is to provide an effective shield to first responders and other medical practitioners against infection and contamination from contaminated bodily fluids during a suctioning procedure.

Still another object is to reduce contamination of the patient's body by bodily fluids during a suctioning procedure.

Another object of the invention is to prevent contamination of equipment being used to render assistance to a patient.

A further object of the invention is to provide a shield during suctioning, irrigation or minor surgical procedures while maintaining a visual oversight of the process.

Technical Solution

The present invention meets the objects of the invention by providing for a clear plastic shield for use with suctioning catheters such as the Yankauer suction instrument. In one embodiment of the invention, the shield is made from a clear resin such as the K-Resin by Chevron Philips Chemical Co. The shield is intended to be single use and disposable. The shield comprises a body having sufficient dimensions to provide a protective barrier between the oral/nasal cavities of the patient and the responder when mounted on a suction catheter. In one preferred embodiment of the invention the body has the general shape of a rhombus with all four sides congruent. In other embodiments, the body may adopt the shape of a parallelogram or other rectangle. The body has a dish-shaped appearance having a bottom surface having a concave profile and a top surface also having a convex profile. The body further comprises a pair of supporting projections that are adapted to support the shield/catheter combination when not in use and to maintain the end of the catheter above the surface upon which the body rests to avoid contamination. As well, the pair of projections provide some frictional resistance to slippage. On the outside surface of the body there is an aperture with a raised collar. The aperture receives a pliable plastic bushing having an aperture, a top flange and bottom flange. The tubular body of the bushing is hourglass shaped to fit within the double beveled aperture of the shield to provide better security within the shield when introducing and extracting whatever device is applied within. The bushing aperture is a bit smaller than the diameter of the medical tool such as a catheter so that once the catheter inserted into the aperture there will be a fluid-tight seal between the catheter and the body of the shield. The seal also provides a frictional grip around the circumference of the catheter while allowing some sliding of the shield up or down the catheter as desired by the responder as well as rotational and angular flexibility.

ADVANTAGEOUS EFFECTS

BEST MODE

Detailed Description of a Preferred Embodiment

Figure 1:
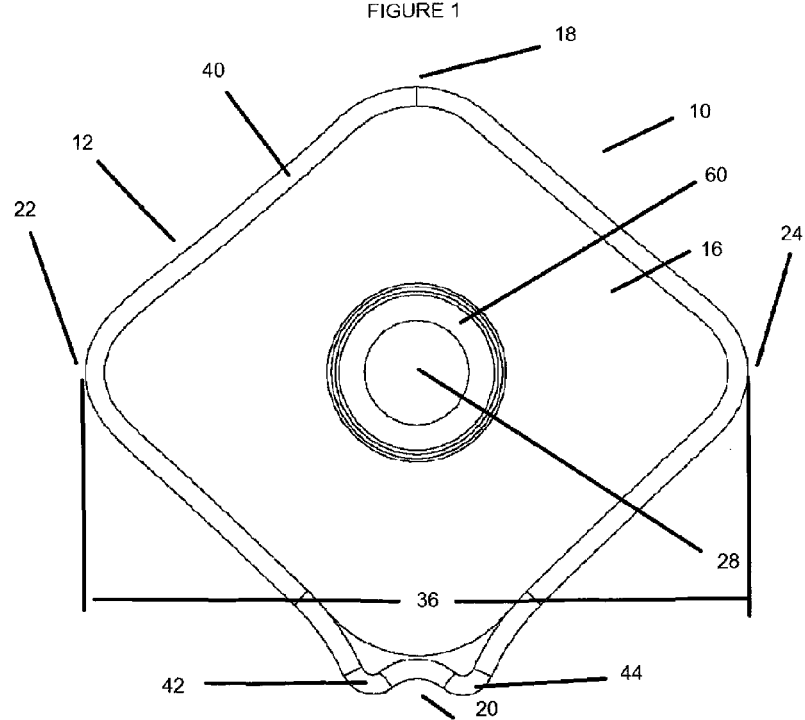
FIG. 1 is a front view of the body of one embodiment of the invention.
Figure 2:
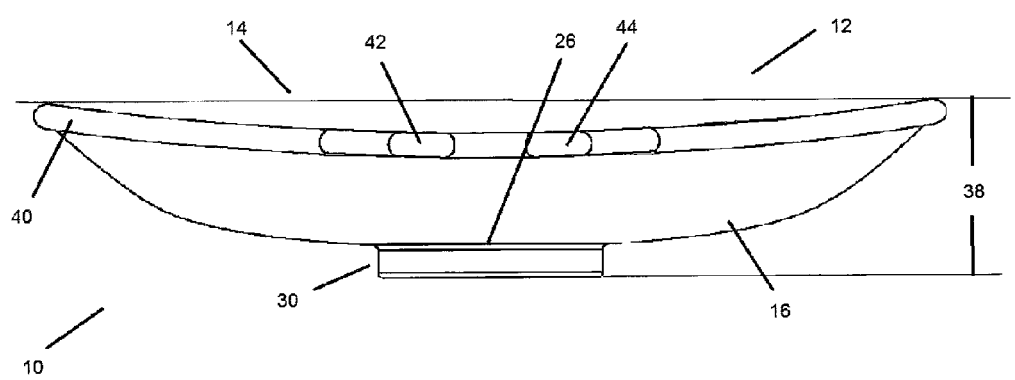
FIG. 2 is an side view of the body of one embodiment of the invention.
Figure 3:
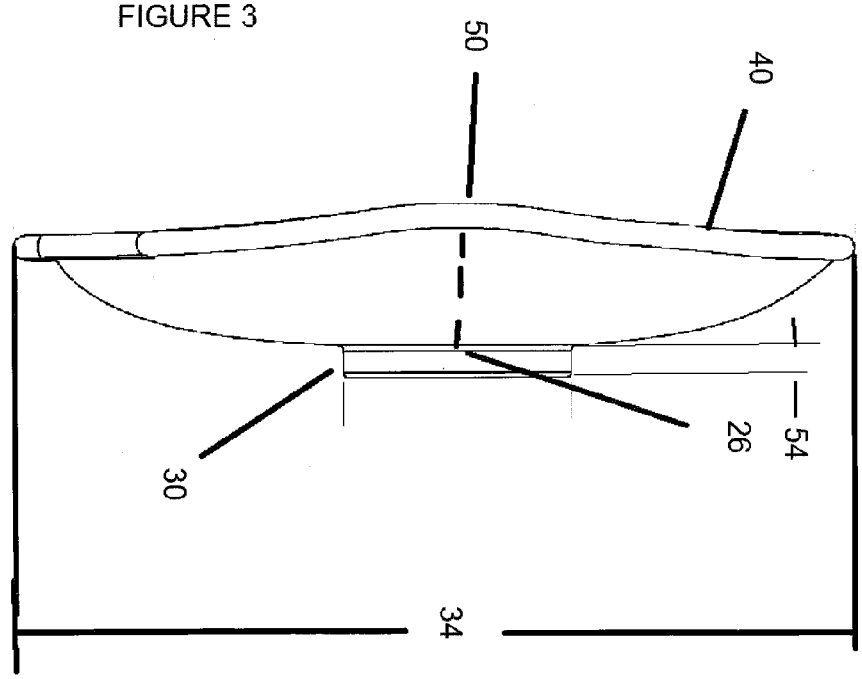
FIG. 3 is another side view of the body of one embodiment of the invention.
Figure 4:
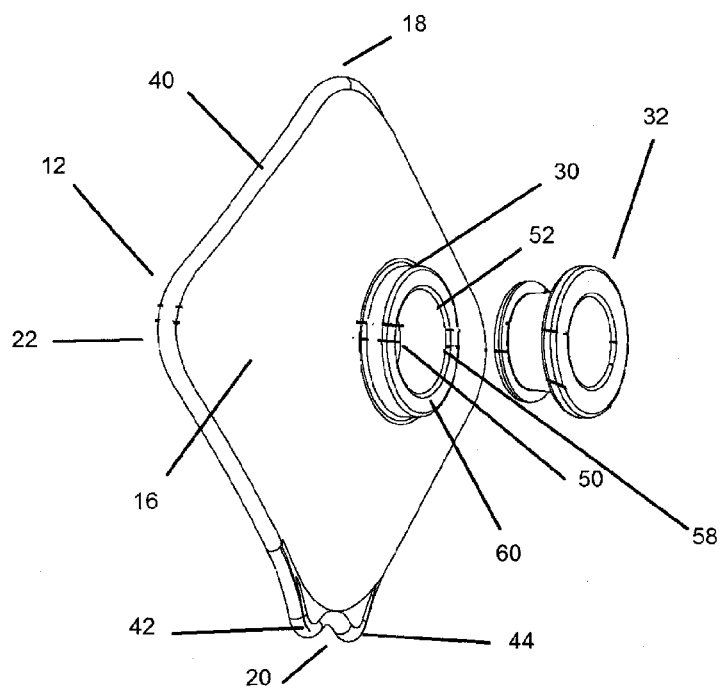
FIG. 4 is a perspective front view of one embodiment of the invention illustrating the aperture seal.
Figure 5:
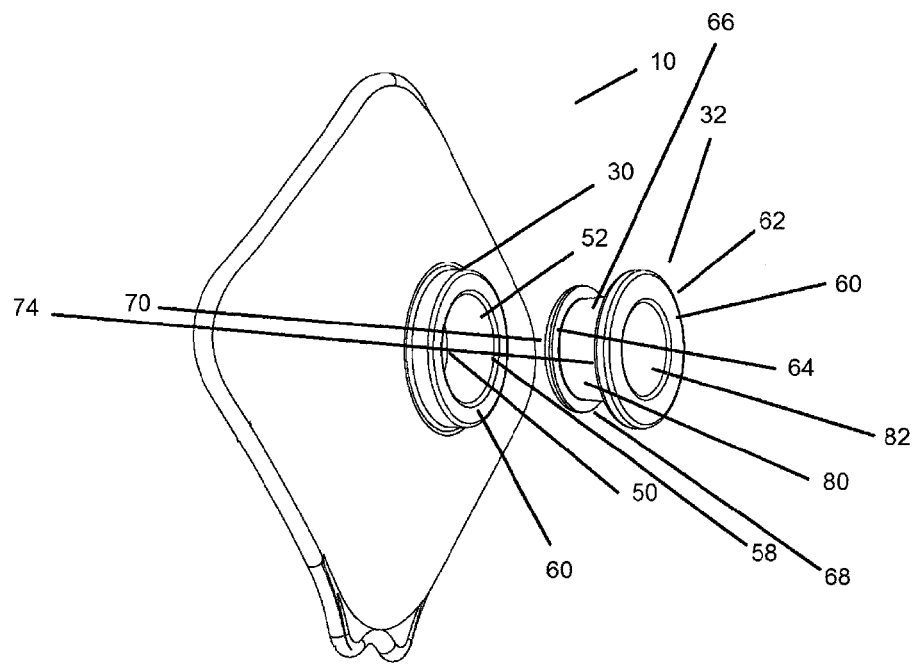
FIG. 5 is the same view as FIG. 4.

Referring to the figures, our invention is a shield 10 for a medical tool to protect a responder against infection by the bodily fluids of a patient and to protect a patient against contamination. The shield 10 comprises a body 12 comprising a generally rhomboid shape and is dimensioned to provide effective shielding to responder against bodily fluids projected by a patient. The body 12 further comprises a concave inside surface 14 and a convex outside surface 16. The body has a top curved end 18 and a bottom curved end 20, a left curved end 22 and a right curved end 24. The body 12 further comprises a outside apex 26 having an aperture 28 centrally disposed at the outside apex 26. A raised collar 30 depends outwards from the apex and is disposed about the aperture 28. A bushing 32 is disposed within the raised collar for receiving and grasping an aid medical tool.

Still referring to the figures, the body 12 further comprises a height 34, a width 36 and a depth 38. The width 36 is longer than the height 38 to achieve the rhomboid shape of the body. The body 12 is formed from a transparent material so that the medical tool is visible to an operator. The transparent material is a thermoplastic material. Alternatively the body can be made from a clear resin such as the K-Resin by Chevron Philips Chemical Co.

A rounded bead 40 disposed around the body 12 to stiffen the body and eliminate sharp edges that might otherwise expose the patient and the responder to cuts and infection. The rounded bead 40 comprises a first projection 42 and a second projection 44 depending from the body bottom end 20 for supporting the body in a vertical position. This also supports the contaminated end of the tool away from the patient if the body is set upon the body of the patient. As well this provides isolation of the working end of the tool from any contaminated surface upon which it rests.

The raised collar 30 has a first portal 50 at the inside concave surface 14 of the body 12 and a second portal 52 raised a distance 54 from the outside convex surface 16. The first portal 50 has a first portal shoulder area 56 (not shown). The collar has a collar height 54 and a collar inside surface 58 between the first portal 50 and said second portal 52. The bushing 32 is disposed between the first portal 50 and the second portal 52. The second 52 portal has an adjacent second portal shoulder 60. The bushing 32 comprises a top flange 62, a bottom flange 64 and a tube 66 disposed between the top flange 62 and the bottom flange 64. The bottom flange 64 has a bottom flange top surface 68 and a bottom flange bottom surface 70. The bottom flange 64 is inserted into the collar 30 so that the bottom flange 64 penetrates into the concave inside surface 14 and so that the bottom flange top surface 68 abuts the adjacent first portal shoulder area. The top flange 62 comprises a top flange bottom surface 74 and an adjacent second portal shoulder 76. The top flange bottom surface 74 abuts against the adjacent second portal shoulder 60. The tube 66 has a height that is slightly less than the collar height 54 and comprises an elastic material. The tube further comprises an outside surface 80 for stretched abutment against the collar inside surface 58 so that the bushing bottom flange 64 is tensioned against the first portal shoulder area and the bushing top flange 62 is tensioned against the adjacent second portal shoulder 60 thereby maintaining the bushing firmly secure within the collar. In addition this internal interface is hourglass shaped so as to provide maximum security between the bushing and the shield. The tube 66 has an inside surface 82 and an aperture width 84 that is sufficiently dimensioned to accept the medical tool in frictional engagement with the inside surface so that the medical tool is retained firmly within the tube and remains dexterous therein. The bushing is also disposable.

Figure 6:
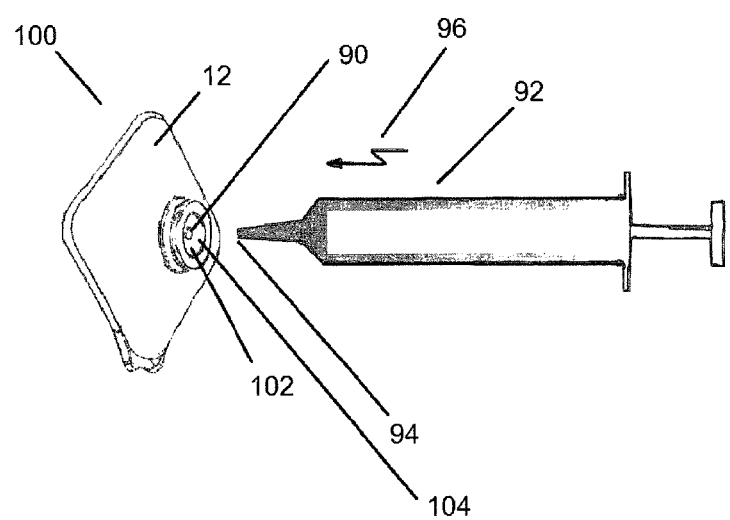
FIG. 6 is a view of the invention used with a syringe.

Referring to FIG. 6, there is another embodiment of the invention 100 comprising a body 12 and a bushing 102. The bushing has a small aperture 90 within a diaphragm 104 instead of the large aperture 28 depicted in FIG. 1. The small aperture 90 has a width that is slightly smaller than the width 94 of the end of the syringe 92. In this way there is a seal between the syringe end 92 and the bushing 102. The aperture 90 within the diaphragm 104 may be sealed with a thin membrane or a weakened area of the diaphragm so that the end of the syringe can pierce the diaphragm weakened area when pushed 96 into the diaphragm.

Figure 7:
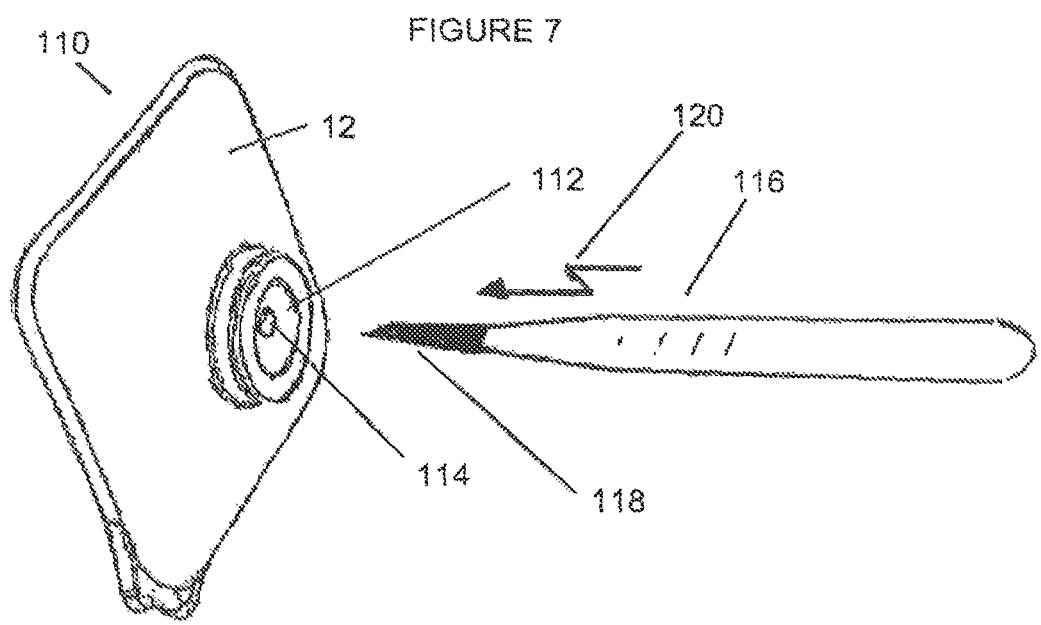
FIG. 7 is a view of the invention used with a scalpel.

Referring to FIG. 7, there is shown another embodiment of the invention 110 comprising a body 12 and a bushing 112. The bushing 112 has an aperture 114. In this embodiment the medical tool 116 is a scalpel having a blade 118. The blade of the scalpel can be forced in direction 120 into the aperture so that the aperture compresses around the handle of the blade and forms a seal between the handle and the bushing.

Figure 8:
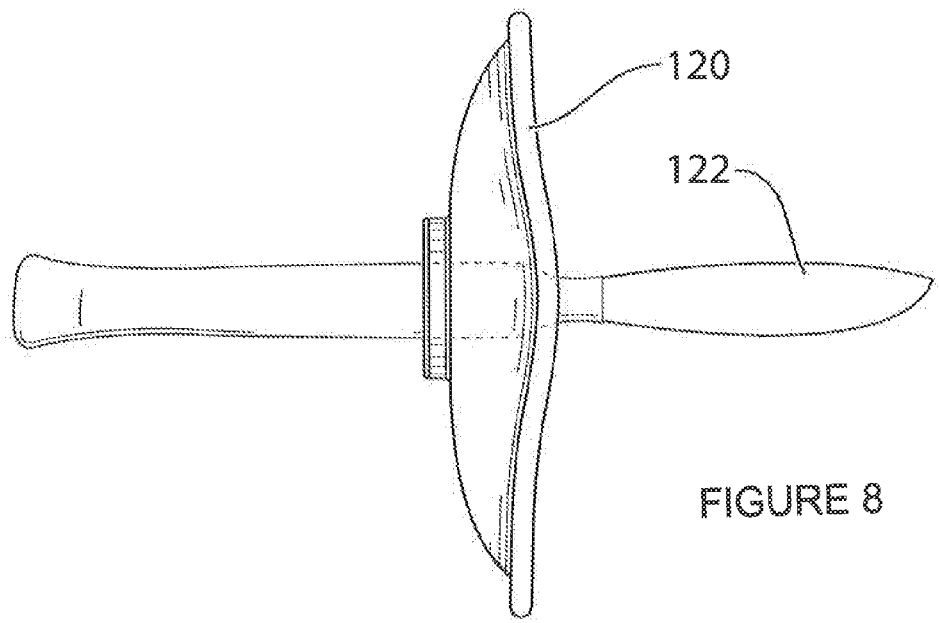
FIG. 8 is a view of an embodiment of the invention in use with a scalpel.

Referring to FIG. 8 there is shown an embodiment of the invention 120 used in a variety of applications comprising a scalpel 122, a syringe 124, an aspirator 126 and a catheter 128.

Although the description above contains much specificity, these should not be construed as limiting the scope of the invention but as merely providing illustrations of the presently preferred embodiment of this invention. Thus the scope of the invention should be determined by the appended claims and their legal equivalents.

MODE FOR INVENTION

FIG. 8 is a view of an embodiment of the invention in use with a scalpel.

Figure 9:
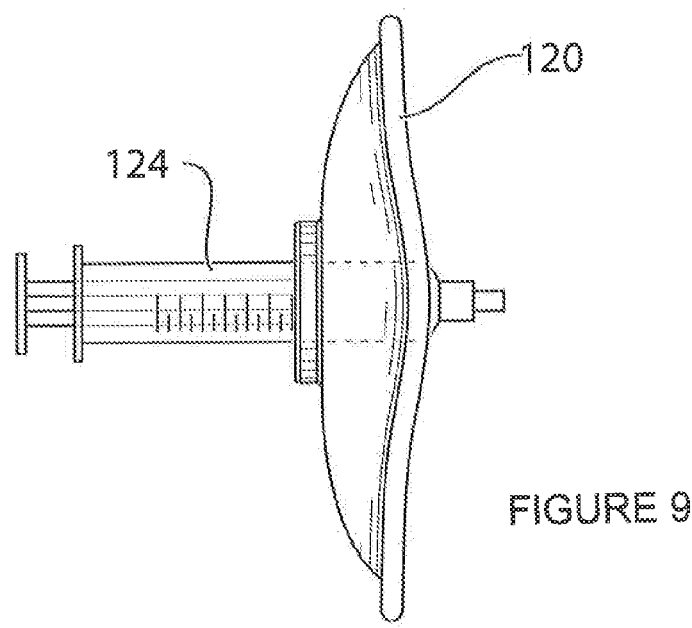
FIG. 9 is a view of an embodiment of the invention in use with a syringe.

FIG. 9 is a view of an embodiment of the invention in use with a syringe.

Figure 10:
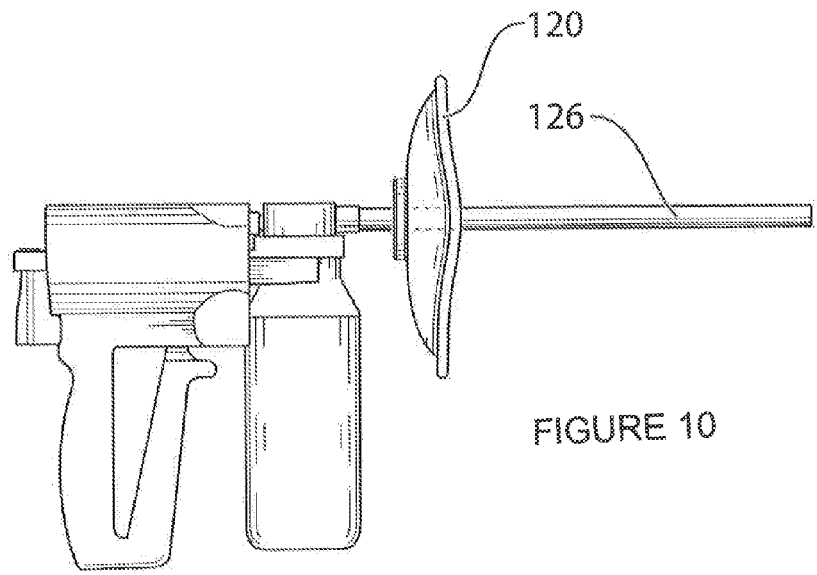
FIG. 10 is a view of an embodiment of the invention in use with an aspirator.

FIG. 10 is a view of an embodiment of the invention in use with an aspirator.

Figure 11:
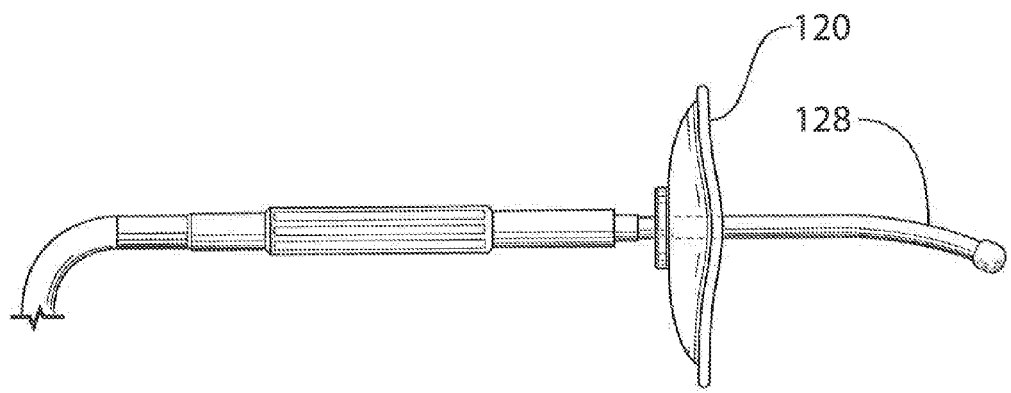
FIG. 11 is a view of an embodiment of the invention in use with a Yankauer suction catheter.

FIG. 11 is a view of an embodiment of the invention in use with a Yankauer suction catheter.

The invention claimed is:

1. A shield for a medical tool, said shield comprising:
  a. a body comprising a generally rhomboid shape and dimensioned to provide effective shielding to a responder against bodily fluids projected by a patient;
  b. the body further comprising a concave inside surface and a convex outside surface, a top curved end and a bottom curved end, a left curved end and a right curved end;
  c. the body further comprising an outside apex and wherein an aperture is centrally disposed at said outside apex;
  d. a raised collar depending outwards from the outside apex and disposed around said aperture; and,
  e. a bushing disposed within said raised collar for receiving and grasping said medical tool, wherein:
  f. the raised collar has a first portal at the inside concave surface of the body and a second portal raised a distance from the outside convex surface, and said first portal has a first portal shoulder area and further the collar has a collar height and a collar inside surface between the first portal and said second portal and further said collar inside surface has an hourglass profile in cross-section;

g. said bushing is disposed between said first portal and said second portal, and the second portal has an adjacent second portal shoulder; and h. the bushing comprises a top flange, a bottom flange and a tube disposed between said top flange and said bottom flange, and further said tube has an hourglass profile in cross-section to cooperate with said collar inside surface hourglass profile in cross-section so that when an axial force is exerted upon a tool set within the tube, said axial force and any displacement of the tube is resisted by said cooperating hourglass profiles.

2. The shield of claim 1 wherein the body further comprises a height, a width and a depth and wherein said width is longer than said height.

3. The shield of claim 2 wherein the body is formed from a transparent material so that the medical tool is visible to said responder.

4. The shield of claim 3 wherein said transparent material is one of a thermoplastic and a resin.

5. The shield of claim 1 further comprising a rounded bead disposed around the perimeter of the body to stiffen the body and eliminate sharp edges.

6. The shield of claim 5 wherein said rounded bead comprises a first projection and a second projection depending from said body bottom end for supporting the body in a vertical position and for providing frictional engagement between the body and a surface upon which the body is placed to prevent slippage of the body.

7. The shield of claim 1 wherein the bottom flange has a bottom flange top surface and a bottom flange bottom surface and is inserted into the collar so that the bottom flange penetrates into the concave inside surface and so that said bottom flange top surface abuts said first portal shoulder area.

8. The shield of claim 7 wherein the top flange comprises a top flange bottom surface and a top flange top surface and wherein said top flange bottom surface abuts against said adjacent second portal shoulder.

9. The shield of claim 8 wherein said tube has a height that is slightly less than said collar height and further wherein said bushing comprises an elastic material.

10. The shield of claim 9 wherein said tube comprises an outside surface for stretched abutment against said collar inside surface so that the bushing bottom flange is tensioned against the first portal shoulder area and the bushing top flange is tensioned against the adjacent second portal shoulder thereby maintaining the bushing firmly secure within the collar.

11. The shield of claim 10 wherein the tube has an inside surface and an aperture width that is sufficiently dimensioned to accept the medical tool in frictional engagement with said inside surface so that the medical tool is retained firmly within the tube and is dexterous therein.

12. The shield of claim 11 wherein the bushing is disposable.

13. The shield of claim 1 wherein the medical tool is one of a suction catheter, a scalpel, a syringe and an irrigation instrument.

14. A shield for a medical tool, said shield comprising:

a. a body comprising a height, a width and a depth and wherein said width is longer than said height and wherein said body comprises a generally rhomboid shape and is dimensioned to provide effective shielding to a responder against bodily fluids projected by a patient;

b. the body further comprising a concave inside surface and a convex outside surface, a top curved end and a bottom curved end, a left curved end and a right curved end and wherein the body is formed from a transparent material so that the medical tool is visible to said responder;

c. the body further comprising an apex on said convex outside surface and wherein an aperture is centrally disposed at said apex and further wherein a rounded bead is disposed around the body to stiffen the body and eliminate sharp edge said rounded bead comprising a first projection and a second projection depending from said body bottom end for supporting the body in a vertical position and for providing a frictional engagement between said first and said second projections and a surface upon which the body rests;

d. a raised collar depending outwards from the apex and disposed about said aperture, wherein said raised collar has a first portal at the inside concave surface of the body and a second portal raised a distance from the outside convex surface, and wherein said first portal has a first portal shoulder area and further wherein the collar has a collar height and a collar inside surface between the first portal and said second portal, wherein said collar inside surface has an hourglass profile in cross-section; and, e. a bushing disposed within said raised collar for receiving and frictionally grasping said medical tool, wherein said bushing is disposed between said first portal and said second portal, and wherein the second portal has an adjacent second portal shoulder and comprises a top flange, a bottom flange and a tube disposed between said top flange and said bottom flange, and wherein said tube has an outside surface having an hourglass cross-sectional profile matching said collar inside surface hourglass profile.

15. The shield of claim 14 wherein the bottom flange has a bottom flange top surface and a bottom flange bottom surface and is inserted into the collar so that the bottom flange penetrates into the concave inside surface and so that said bottom flange top surface abuts said first portal shoulder area and wherein the top flange comprises a top flange bottom surface and a top flange top surface and wherein said top flange bottom surface abuts against said adjacent second portal shoulder.

16. The shield of claim 15 wherein said tube has a height that is slightly less than said collar height and further wherein said bushing comprises an elastic material and further wherein said tube outside surface is disposed for stretched abutment against the collar inside surface so that the bushing bottom flange is tensioned against the first portal shoulder area and the bushing top flange is tensioned against the adjacent second portal shoulder thereby maintaining the bushing firmly secure within the collar, and further wherein the hourglass cross-sectional profile of the collar inside surface cooperates with the tube hourglass cross-sectional profile to resist an axial force on an inserted medical tool so that there is no displacement of the tube within the collar.

17. The shield of claim 16 wherein the tube has an inside surface and an aperture width that is sufficiently dimensioned to accept the medical tool in frictional engagement with said inside surface so that the medical tool is retained firmly within the tube and is dexterous therein.

\* \* \* \* \*